United States Patent [19]

Cook et al.

[11] Patent Number: 4,852,967

[45] Date of Patent: Aug. 1, 1989

[54] EVANESCENT WAVE SENSORS

[75] Inventors: Thomas A. Cook, Corning; Walter F. Love, Horseheads, both of N.Y.; Rudolf E. Slovacek, Norfolk, Mass.

[73] Assignee: Ciba Corning Diagnostics Corp., Medfield, Mass.

[21] Appl. No.: 843,637

[22] Filed: Mar. 25, 1986

[51] Int. Cl.[4] .................................................. G02B 6/02
[52] U.S. Cl. .................................. 350/96.29; 350/96.15
[58] Field of Search ............... 350/96.15, 96.16, 96.18, 350/96.29; 250/227

[56] References Cited

U.S. PATENT DOCUMENTS

| | | | |
|---|---|---|---|
| 3,604,927 | 9/1971 | Hirschfeld | 356/38 X |
| 4,009,382 | 2/1977 | Nath | 350/96.32 X |
| 4,447,546 | 5/1984 | Hirschfeld | 250/227 X |
| 4,558,014 | 12/1985 | Hirschfeld et al. | 250/227 X |
| 4,600,310 | 7/1986 | Cramp et al. | 350/96.29 X |

Primary Examiner—John D. Lee
Assistant Examiner—John Ngo
Attorney, Agent, or Firm—William G. Gosz

[57] ABSTRACT

The present invention relates to a novel evanescent wave sensor which can have a high numerical aperture and is capable of being used in various forms of optically-based assays. Unlike previous fiber optical devices, the present sensors do not use any cladding at the contact points.

8 Claims, 3 Drawing Sheets

EVANESCENT WAVE SENSORS

TECHNICAL FIELD

The present invention relates to a novel evanescent wave sensor which can have a high numerical aperture and is capable of being used in various forms of optically-based assays. Unlike previous fiber optical devices, the present sensors do not use any cladding at the contact points.

BACKGROUND ART

The use of evanescent wave phenomena as a detection means in optically-based assays is known in the art. The total reflective spectroscopy (TRS) techniques of Myron Block (U.S. Pat. No. 4,447,546 and U.S. Pat. No. 4,558,014) use an evanescent wave to both excite a fluorescently tagged analyte and to detect the resulting fluorescence. As disclosed therein, the sensors are comprised of optical telecommunication-type fibers which have a core surrounded by a cladding, at least where the fiber is held. Another portion of the fiber has a bare (or naked) core which is coated with an immunochemically reactive substance, i.e., an antigen or an antibody. This basic sensor configuration can be found in other disclosures such as WO 83/01112 to T. Carter et.al. and U.S. Ser. No. 652,714 to D. Keck et. al.

The presence of a cladding or means to insure energy isolation has both positive and negative effects. On the positive side, the cladding prevents mode stripping where the fiber is held. This is especially important when one is using a sensor for evanescent wave detection because in some cases, i.e., fluorescent measurements, less than one percent of the excitation energy will return as a signal. Thus, cladding has been required to insure that signal stripping does not occur. However, the negative consequences of this approach include manufacturing difficulties in selectively stripping or adding cladding to a fiber and the inherent limitation the cladding imposes on the critical angle or numerical aperture (NA) of the sensor.

The critical angle $\theta_c$ of a fiber optic or waveguide device, in general, and an evanescent wave sensor, in particular, is determined by the differences between the refractive indices of the launching medium, propagating medium, and the surrounding medium. It refers to the maximum angle, with respect to the longitudinal axis of the waveguide, at which light can enter the waveguide and still be retained and propagated by the waveguide. In practice, the art refers more often to the numerical aperture (NA) of a waveguide rather than the critical angle. Mathematically, the relationship is as follows:

$$NA = N_0 \sin\theta_c = (N_1^2 - N_2^2)^{1/2}$$

Where
$N_0$ = refractive index of the launching medium
$N_1$ = refractive index of the propagating medium
$N_2$ = refractive index of the surrounding medium.
(See FIG. 1).

DISCLOSURE OF THE INVENTION

The present invention relates to evanescent wave sensors that are useful in optically-detectable assays, including such formats as immunoassays, enzymatic clinical chemistry assays, molecular probe hybridization assays, cell measurements, and dye-based pH/blood gas assays. However, the use of these sensors is not limited to aqueous solutions, but rather can be used in gaseous or non-aqueous environments. The labels or tags for these assays include fluorescent, chemiluminescent, and absorptive compounds well known in the art.

The sensor is comprised of two parts, a light conducting means and a holding means. The former is a electromagnetic wave-propagating device of numerous configurations; e.g., cylindrical or planar. Functionally, it carries light along the waveguide to a point where the propagating surface of the waveguide (and, of course, the accompanying evanescent wave) contacts optically-detectable or labelled analyte.

The unexpected novelty of the present sensor lies in the use of a holding means which can contact the light conducting member at the wave-propagating surface, ergo, the latter does not require a conventional cladding or energy isolation means attached thereto where it is held. The holding means contacts the wave-propagating surface. There are three general cases, one of which is thickness dependent.

In cases where the seal material is optically transmissive and has an index of refraction ($N_3$) which is greater than that of the medium surrounding the light conducting member, mode stripping, i.e., the loss of transmitted light due to contact pertubation, is minimized by controlling the thickness at the contact points. The thickness of the contact points should be less than Lambda ($\Lambda$) divided by the optical parameter (f), where $\Lambda$ equals the cross-sectional thickness of the light conducting member divided by the tangent of the propagation angle theta ($\theta$). Theta is less than or equal to the critical angle of the light conducting member) and, as shown in FIG. 2, f being a material dependent parameter associated with the light transmission across the waveguide/seal interface and varying between one and zero.

Optical power loss in seals can be independent of thickness in cases where either the seal or the contact surfaces of the light conducting member are made of either optically transmissive or optically reflective materials. In the former case, the seal is made of a material having an index of refraction less than both the light conducting member and the medium to be sampled. While in the latter case the seal or the light conducting member has a reflective surface at the interface between the two.

Without conventional types of cladding, the NA of these sensors becomes dependent on the difference between the refractive indices of the light conducting member and the surrounding medium, e.g., air or water. Thus, for aqueous-based assays the high end of the sensor NA range is no longer restricted to about 0.3, but can now be extended to 0.6.

The combination of easier manufacturing requirements and expanded capabilities makes the present invention the evanescent wave sensor of choice. Conventional cladding steps are eliminated, and greater NA's mean substantially greater sensor sensitivity. It has been determined experimentally (at sin $\theta_{max}$) that the fluorescent signal associated with free fluorescein varies strongly, approximately equal to $\sin^8 \theta_{max}$, where $\theta_{max}$ is the maximum angle for light launched into the light conducting member.

PREFERRED MODES OF THE INVENTION

Figure 1:
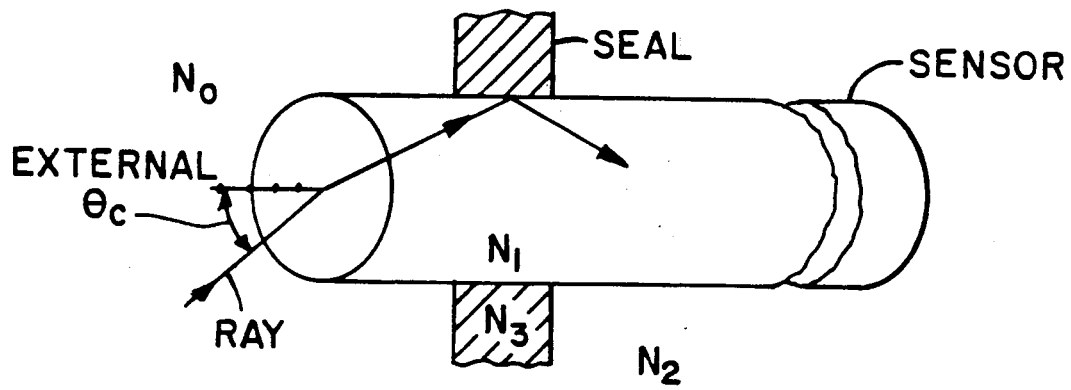
FIG. 1 is a cross-sectional view of the seal of the present sensor.
Figure 2:
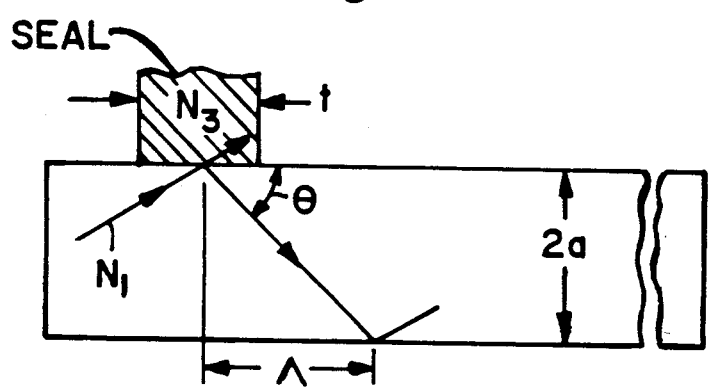
FIG. 2 is a cross-sectional view of the present sensor showing the angle Theta ($\theta$).

The present sensor can be made from a wide selection of materials. Optical glass and plastic are preferred for the light conducting member. The choice can be based on the selected excitation and detection wavelengths, and possible absorption or internal fluorescence interferences at those wavelengths. It should be noted that for the present purposes, "light" also refers to wavelengths outside of the visible spectrum, including the ultraviolet and infrared ranges.

Likewise, the holding means can be made from a variety of materials, however, the choice of material affects the required thickness at the contact points for minimal optical pertubation. The optical transmission of light (T) within the light conducting member is given by the following formula:

$$T = 1 - (tf)/\Lambda$$

where t is the seal thickness, and T varies between zero and one.

Depending upon the relative magnitudes of $N_1$, $N_2$, and $N_3$, ($N_3$ being the refractive index of the seal), several cases can be generated:

TABLE I

| Case | Transmission Conditions | | | Requirements for Minimum Power Loss |
|---|---|---|---|---|
| 1 | $T = 1$ | $f = 0$ | $N_1 > N_2 \geq N_3$ | t is not functional |
| 2 | $0 < T < 1$ | $0 < f < 1$ | $N_1 > N_3 > N_2$ | $(t/\Omega) f << 1$ |
| 3 | $0 < T < 1$ | $f = 1$ | $N_3 = N_1 > N_2$ | $(t/\Omega) << 1$ |
| 4 | $0 < T < 1$ | $0 < f < 1$ | $N_3 > N_1 > N_2$ | $(t/\Omega) f << 1$ |
| 5 | $T \approx 1$ | $f \approx 0$ | $N_1 > N_2$ | t is essentially not functional |

In the first case of Table I, t is not functional, and thus, the thickness of the seal becomes essentially immaterial because the seal maintains the electromagnetic radiation within the light conducting member. In practice, one selects a seal material having an index of refraction lesser than or equal to that of the surrounding medium. The remaining cases probably have greater utility because one selects the seal material with respect to the material used for the light conducting member, and thus, typically, a greater selection of materials is available. In the second case, a polyfluorinated hydrocarbon seal (such as Teflon ®) would be used on a light conducting member which is made of optical glass and which is surrounded by an aqueous solution. Such a seal is preferred because the refractive index of the Teflon ® closely matches that of the aqueous solution.

If other materials such as latex or the light conducting material itself were to be used for seals, and thus $N_3$ is greater than or equal to $N_2$, then the thickness of the seals would have to be limited to the conditions set forth in the third and fourth cases in Table I. For example, where a rubber seal is used on a light conducting member made of optical glass, the power loss is strongly dependent upon the thickness of the seal.

Finally, the last case in Table I refers to sensors wherein f approaches zero, as in the first case. However, the selection of the seal material is no longer based on indices of refraction. Here, the seal is reflective but not optically transmissive. For example, the seal contact surface comprises a mirror-like coating. The coating having been deposited on either the seal surface or the contact surface of the light conducting member.

The shape of the sensor elements is not restricted to one configuration. The light conducting member may be either a solid or hollow, cylindrical or planar surface having any desired thickness. Unlike prior telecommunication fiber sensors, thickness can easily exceed 1000 microns. Likewise the holding means can be suited to both the light conducting member and any associated sensor structures such as protective or sample volume shields, locking means, et al. Of course, the key feature is that the contact points thickness does not exceed the above limits. The points can be distinct or merged into a gripping flange ring.

Preferably the holding means contacts the light conducting member within a set distance (x) from the electromagnetic radiation launching end of the member. This reduces the pertubation effect of the seal when the launched light spot is smaller than the cross section of the light conducting member. Mathematically this distance is defined as $$x = (R_f - R_s)/\tan \theta$$

where
  $R_f$ = one half of the cross-sectional thickness of the member;
  $R_s$ = one half of the cross-sectional thickness of the launched optical spot ($R_f > R_s$); and
  $\theta$ = angle theta (as described above).

Figure 3:
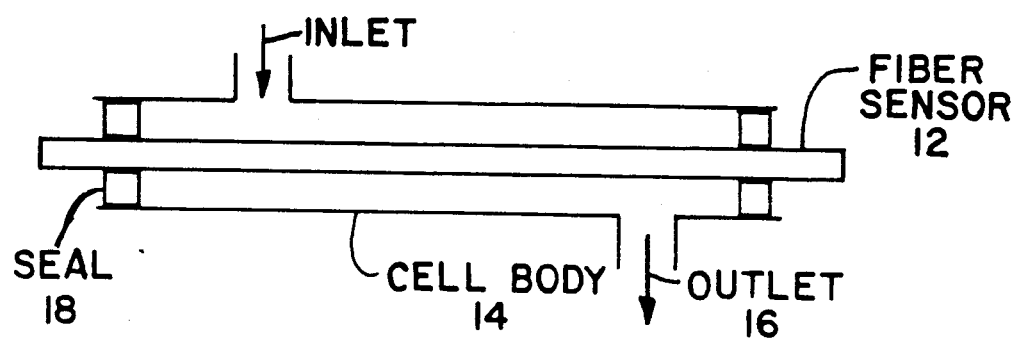
FIG. 3 is a cross-sectional view of a preferred form of the present sensor.

In practice, a typical immunoassay sensor would be configured as shown in FIG. 3. A sensor (10) comprises a light conducting member or waveguide (12) made of optical glass (n=1.46) and having diameter of 500 microns and a length of 7 cm. Placed about the fiber is a tubular sample chamber (14) having inlet and outlet means (16) of greater diameter and lesser length (5 cm.). Alternatively, the sample chamber can be greater in length with a recessed fiber, the caps extending inwardly to grip the fiber. The holding means is comprised of molded end caps (18) made from Teflon $^R$ (n=1.34) which are designed and shaped to grip the chamber end, forming a watertight seal, and to contact circumferentially the light conducting member with a thin contact distance for minimal pertubation. (See Table I).

Those skilled in the art recognize the wide applications of such sensors. For example, IR or UV absorption of the evanescent wave can yield identification and concentration of many organic liquids, the sensor serving as a monitor for chemical process control.

The effect of excessively thick contact points can be readily seen as follows, where the observed fluorescent signal decreases from 900 to 51 cps with an increase in seal thickness of 0.14 to 2.00 mm.:

TABLE II

| EVANESCENT WAVE SENSOR SEAL MATERIALS | | | |
|---|---|---|---|
| | Rubber | Latex | Teflon ® |
| Refractive Index | 1.51 | 1.51 | 1.34 |
| Seal Thickness (mm) | 2.00 | 0.14 | 0.25 |
| Fluorescent signal (cps) | 51 | 900 | 8000 |

The use of both a low-index material such as Teflon®, and thin contact distance gives an extremely well-optimized signal. (The above results have been obtained using an aqueous solution of fluorescein at $10^{-6}$ molar.)

Figure 4:
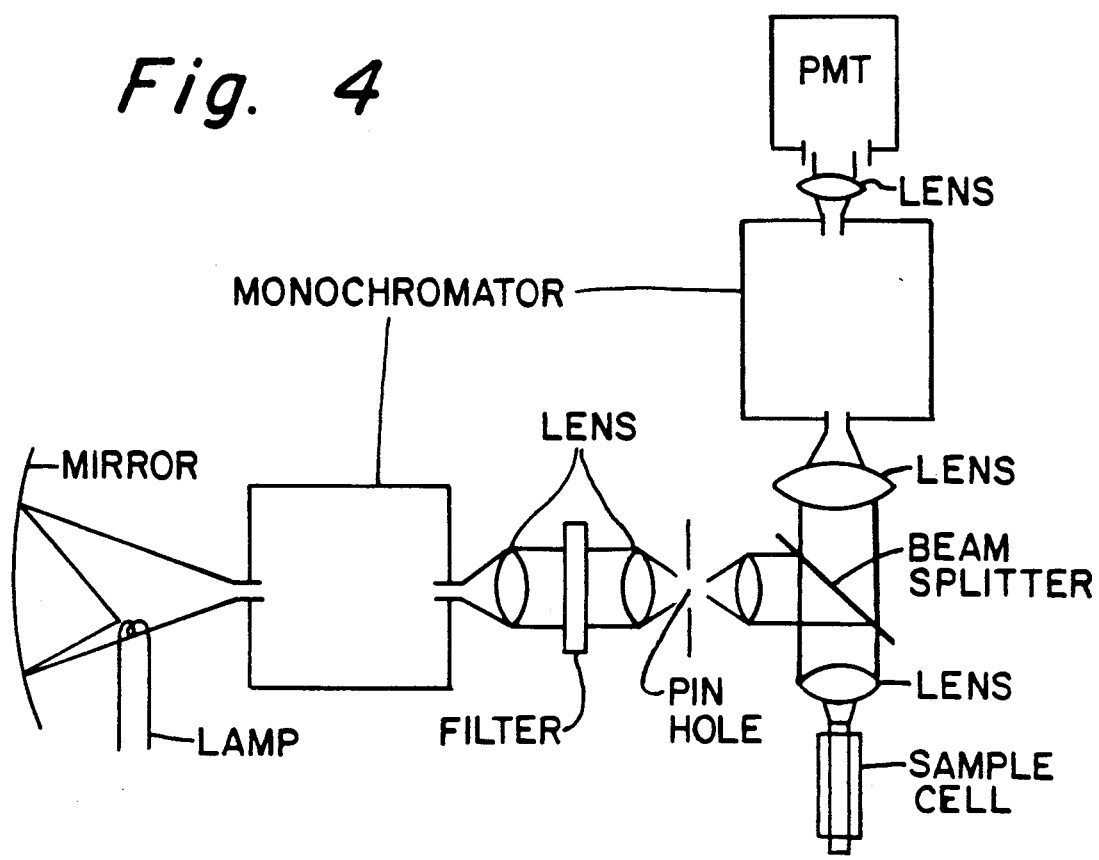
FIG. 4 is a diagram of an optical system for use with the present sensor.

The use of the present evanescent wave sensor is illustrated by the two examples described below both of which used an optical system as shown in FIG. 4.

SOLUTION FLUORIMETRY

Figure 5:
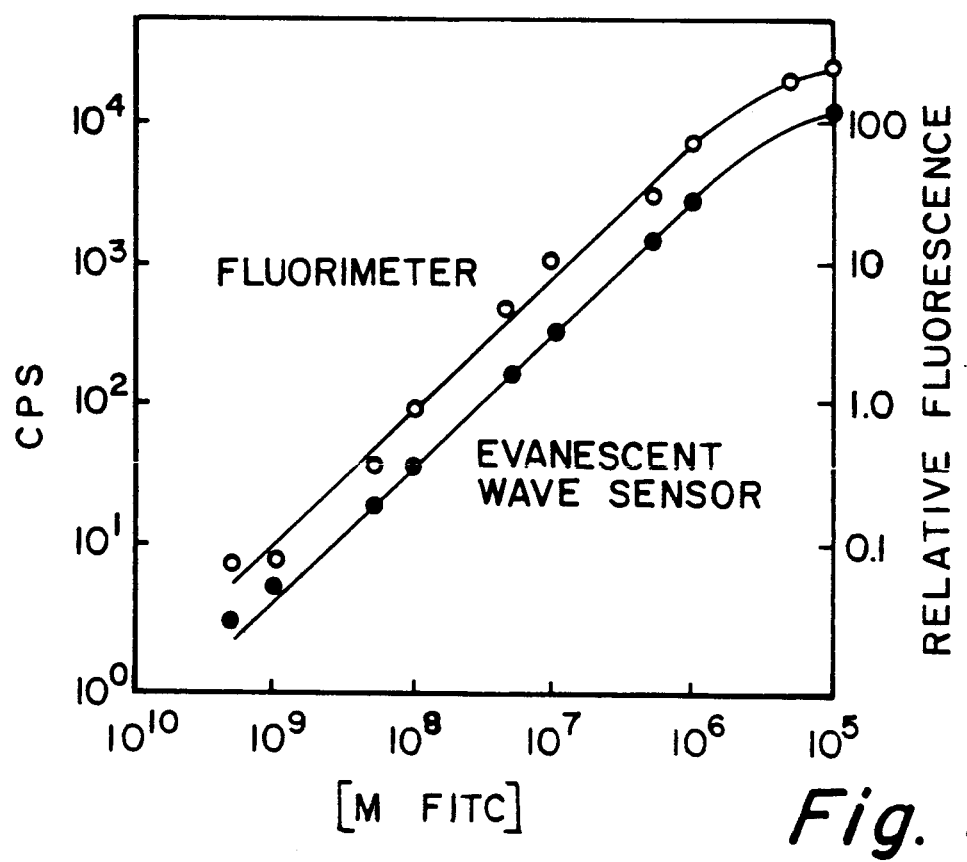
FIG. 5 is a graph comparing the sensitivity of the present sensor versus conventional solution fluorimetry.

In FIG. 5, aqueous solutions containing various concentrations of fluorescein isothiocyanate (FITC) were placed in the sampling chamber surrounding a fiber. Using 490nm excitation light and detecting 525nm fluorescent emission as cps with a photon counter, the relation between fluorescent signal and FITC concentration was established. This is shown to correspond well with the fluorescence versus concentration curve observed with a commercial conventional solution cuvette fluorimeter (Perkin Elmer Model 650-40).

IMMUMOASSAY

Figure 6:
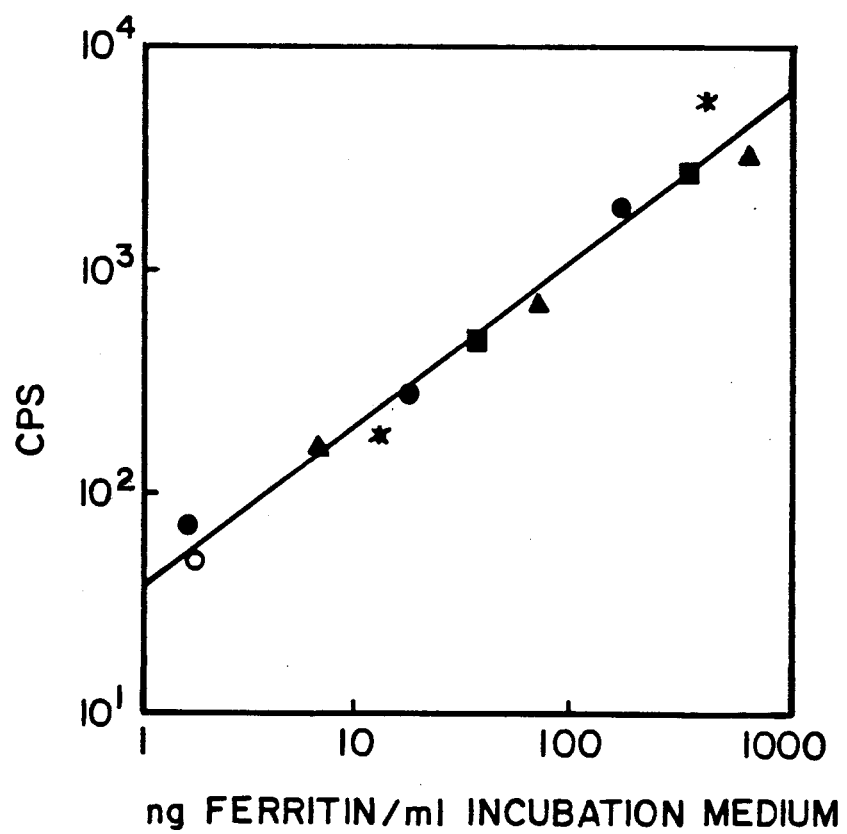
FIG. 6 is a graph showing a fluoroimmunoassay performed with the present sensor.

In FIG. 6, a fluorimeteric immunoassay was constructed for the clinically relevant analyte ferritin using fiber sensors in which the glass fiber component had been previously coupled to anti-ferritin antibodies through the art described in (Weetall Patent U.S. Pat. No. 3,652,271). The sensors were then incubated with various concentrations of ferritin (to produce an immunological binding reaction), washed, then incubated with a secondary ferritin antibody which was labelled with FITC. The proportion of bound labelled antibody gave rise to an increased level of fluorescent signal (as expressed in cps), which is proportional to the amount of ferritin in a sample. The assay range is of clinical relevance while the assay could be performed in 20 minutes or less.

It should be apparent to one having ordinary skill in the art that many variations are possible without departing from the spirit and scope of the invention.

We claim:
1. An evanescent wave sensor comprising:
   (a) a light conducting member having an index of refraction ($N_1$) which is surrounded by a medium having an index of refraction ($N_2$), where $N_1$ is greater than $N_2$; and
   (b) a holding means having an index of refraction ($N_3$), such that $N_3$ is less than $N_2$, which is designed and configured to contact the light conducting member at the wave-propagating surface.
2. The sensor of claim 1 wherein the light conducting member has either a cylindrical or planar configuration.
3. The sensor of claim 1 wherein the medium is an aqueous medium.
4. An evanescent wave sensor as recited in claim 1 wherein the medium is a liquid or gaseous medium.
5. An evanescent wave sensor comprising:
   (a) a light conducting member; and
   (b) a holding means designed and configured:
      (i) to contact the light conducting member at the wave-propagating surface; and
      (ii) to have a thickness at the contact points which is less than Lambda ($\Lambda$) divided by the optical parameter (f), where $\Lambda$ is equal to the cross-sectional thickness of the light conducting member divided by the tangent of the angle Theta ($\theta$), $\theta$ being less than or equal to the critical angle of the light conducting member.
6. The sensor of claim 5 wherein the holding means has an f or 1 and the contact distance (t) for the holding means is smaller than $\Lambda$.
7. The sensor of claim 5 wherein the holding means contacts the light conducting member within a distance (x) from the launching end of the light conducting member, where $x=(R_f-R_s)/\tan\theta$, and $R_f$ equals one-half of the cross-sectional thickness of the light conducting member, $R_s$ equals one-half of the cross-sectional thickness of the launched electromagnetic radiation to be propagated in the waveguide where $R_f$ is greater than $R_s$.
8. The sensor of claim 5 wherein the light conducting member has either a cylindrical or planar configuration.

* * * * *